United States Patent [19]

Brown et al.

[11] Patent Number: 5,629,287
[45] Date of Patent: May 13, 1997

[54] DEPOT FORMULATIONS

[75] Inventors: Robert Brown; Gordon Blun, both of Middlesex, United Kingdom

[73] Assignee: University College London, London, England

[21] Appl. No.: 424,582

[22] Filed: Apr. 17, 1995

Related U.S. Application Data

[63] Continuation of Ser. No. 90,079, Jul. 16, 1993, abandoned.

[30] Foreign Application Priority Data

Jan. 18, 1991 [GB] United Kingdom ............ 9101183

[51] Int. Cl.$^6$ ............................................. A61K 38/16
[52] U.S. Cl. .................... 514/8; 530/380; 530/382; 530/385
[58] Field of Search ....................... 530/380, 382, 530/385; 514/8

[56] References Cited

U.S. PATENT DOCUMENTS

| | | |
|---|---|---|
| 4,885,295 | 12/1989 | Bell . |
| 4,955,892 | 9/1990 | Daniloff . |
| 4,973,466 | 11/1990 | Reich ............................ 424/426 |
| 4,981,841 | 1/1991 | Gibson .......................... 514/2 |
| 4,983,580 | 1/1991 | Gibson .......................... 514/2 |
| 5,013,732 | 5/1991 | Bell . |
| 5,036,056 | 7/1991 | Kludas ........................... 514/54 |
| 5,043,288 | 8/1991 | Motsenbocker . |
| 5,043,429 | 8/1991 | Zimmerman . |
| 5,053,388 | 10/1991 | Gibson et al. ................... 514/2 |
| 5,104,856 | 4/1992 | Esko et al. . |
| 5,120,828 | 6/1992 | Charonis . |
| 5,266,328 | 11/1993 | Skubitz et al. ................. 424/427 |
| 5,270,300 | 12/1993 | Hunziker ....................... 514/12 |

FOREIGN PATENT DOCUMENTS

| | | |
|---|---|---|
| 240031 | 10/1987 | European Pat. Off. . |
| 312208 | 4/1989 | European Pat. Off. . |
| 340628 | 11/1989 | European Pat. Off. . |
| 362526 | 4/1990 | European Pat. Off. . |
| 376189 | 7/1990 | European Pat. Off. . |
| 384362 | 8/1990 | European Pat. Off. . |
| 221977 | 8/1990 | European Pat. Off. . |
| 386906 | 9/1990 | European Pat. Off. . |
| 397633 | 11/1990 | European Pat. Off. . |
| 397635 | 11/1990 | European Pat. Off. . |
| 399806 | 11/1990 | European Pat. Off. . |
| 406428 | 1/1991 | European Pat. Off. . |
| 410006 | 1/1991 | European Pat. Off. . |
| 416250 | 3/1991 | European Pat. Off. . |
| 482649 | 4/1991 | European Pat. Off. . |
| 428266 | 5/1991 | European Pat. Off. . |
| 433817 | 6/1991 | European Pat. Off. . |
| 434836 | 7/1991 | European Pat. Off. . |
| 437622 | 7/1991 | European Pat. Off. . |
| 455263 | 11/1991 | European Pat. Off. . |
| 459577 | 12/1991 | European Pat. Off. . |
| 466505 | 1/1992 | European Pat. Off. . |
| 468181 | 1/1992 | European Pat. Off. . |
| 469985 | 2/1992 | European Pat. Off. . |
| 412951 | 2/1992 | European Pat. Off. . |
| 473564 | 3/1992 | European Pat. Off. . |
| 477833 | 4/1992 | European Pat. Off. . |
| 479071 | 4/1992 | European Pat. Off. . |
| 480189 | 4/1992 | European Pat. Off. . |
| 488583 | 6/1992 | European Pat. Off. . |
| 488258 | 6/1992 | European Pat. Off. . |
| 499544 | 8/1992 | European Pat. Off. . |
| 501233 | 9/1992 | European Pat. Off. . |
| 502496 | 9/1992 | European Pat. Off. . |
| 503301 | 9/1992 | European Pat. Off. . |
| 503583 | 9/1992 | European Pat. Off. . |
| 503646 | 9/1992 | European Pat. Off. . |
| 505749 | 9/1992 | European Pat. Off. . |
| 505868 | 9/1992 | European Pat. Off. . |
| 507187 | 10/1992 | European Pat. Off. . |
| 507604 | 10/1992 | European Pat. Off. . |
| 509120 | 10/1992 | European Pat. Off. . |

(List continued on next page.)

OTHER PUBLICATIONS

Dijke, Peter et al., "Growth Factors for Wound Healing", Biotechnology, vol. 7, pp. 793–798, Aug. 1989.
Baxter, Robert et al., "Glycosaminoglycans inhibit formation . . . ", Biochem. J., vol. 271, pp. 773–777, 1990.
Sommer, A et al., "Modern Concepts of Insulin–Like Growth Factors", Ed. Martin Spencer, Elsevier Publishers, pp. 715–728, Jan. 1991.
Mueller, Reid et al., "Modern Concepts of Insulin–Like Growth Factors", Ed. Martin Spencer, Elsevier, pp. 185–192, Jan. 1991.
Simmons, "Evaluation of collagen cross–linking techniques for the stabilization of tissue matrices", Biotechnol–Appl–Biochem., 1993 Feb; 17 (Pt 1):23–9.
Freed, "Survival of implanted fetal dopamine cells and neurologic improvement 12 to 46 months after transplantation for Parkinson's disease", N. Engl. J. Med., 1992 Nov. 26; 327(22):1549–55.
Gershon, "Compliance and ultimate strength of composite arterial prostheses", Biomaterials, 1992; 13(1):38–43.
Ricci, "In–vitro tendon cell growth on synthetic fiber implant materials:biological implications", Bull. Hosp. Jt. Dis. Orthop. Inst., 1990 Fall; 50(2):126–38.
Matsuda, "Development of a novel artificial matrix with cell adhesion peptides for cell culture and artificial and hybrid organs", ASAIO. Trans. 1989 Jul.–Sep.; 35(3):677–9.
Jakobson, "A simple method for shell–less cultivation of chick embryos", Pharmacol–Toxicol, 1989 Feb.; 64(2):193–5.
Brown, "Therapeutic Uses of Cell–Matrix Adhesive Protein", Current Opinion in Therapeutic Patents, Aug. 1993, pp. 1117–1140.

*Primary Examiner*—Chhaya D. Sayala
*Attorney, Agent, or Firm*—Cushman Darby & Cushman IP Group Pillsbury Madison & Sutro LLP

[57] ABSTRACT

A depot formulation comprising fibronectin or a fragment thereof, a growth factor binding agent linked thereto and growth factor bound to the binding agent is used to promote wound healing in combination with macroscopically oriented cell adhesion proteins, the depot formulations allow the healing process to be directed to afford stronger or more cosmetically acceptable results.

14 Claims, No Drawings

FOREIGN PATENT DOCUMENTS

| Number | Date | Country |
|---|---|---|
| 509517 | 10/1992 | European Pat. Off. . |
| 510483 | 10/1992 | European Pat. Off. . |
| 512301 | 11/1992 | European Pat. Off. . |
| 512916 | 11/1992 | European Pat. Off. . |
| 514721 | 11/1992 | European Pat. Off. . |
| 514970 | 11/1992 | European Pat. Off. . |
| 517174 | 12/1992 | European Pat. Off. . |
| 517182 | 12/1992 | European Pat. Off. . |
| 519901 | 12/1992 | European Pat. Off. . |
| 522606 | 1/1993 | European Pat. Off. . |
| 526756 | 2/1993 | European Pat. Off. . |
| 527056 | 2/1993 | European Pat. Off. . |
| 529659 | 3/1993 | European Pat. Off. . |
| 529858 | 3/1993 | European Pat. Off. . |
| 531978 | 3/1993 | European Pat. Off. . |
| 8803810 | 6/1988 | WIPO . |
| 8904153 | 5/1989 | WIPO . |
| 8904172 | 5/1989 | WIPO . |
| WO8905342 | 6/1989 | WIPO . |
| WO8910135 | 11/1989 | WIPO . |
| 9006767 | 6/1990 | WIPO . |
| WO9008833 | 8/1990 | WIPO . |
| WO9011365 | 10/1990 | WIPO . |
| WO9012033 | 10/1990 | WIPO . |
| WO9012580 | 11/1990 | WIPO . |
| WO9013306 | 11/1990 | WIPO . |
| WO9013566 | 11/1990 | WIPO . |
| WO9013644 | 11/1990 | WIPO . |
| WO9013647 | 11/1990 | WIPO . |
| WO9013653 | 11/1990 | WIPO . |
| WO9014418 | 11/1990 | WIPO . |
| WO9015620 | 12/1990 | WIPO . |
| WO9103252 | 3/1991 | WIPO . |
| WO9101380 | 2/1991 | WIPO . |
| WO9103559 | 3/1991 | WIPO . |
| WO9104058 | 4/1991 | WIPO . |
| WO9105048 | 4/1991 | WIPO . |
| WO9105566 | 5/1991 | WIPO . |
| WO9106315 | 5/1991 | WIPO . |
| WO9107974 | 6/1991 | WIPO . |
| WO9109122 | 6/1991 | WIPO . |
| WO9109614 | 7/1991 | WIPO . |
| WO9109874 | 7/1991 | WIPO . |
| WO9110683 | 7/1991 | WIPO . |
| WO9111462 | 8/1991 | WIPO . |
| WO9112026 | 8/1991 | WIPO . |
| WO9113085 | 9/1991 | WIPO . |
| WO9113093 | 9/1991 | WIPO . |
| WO9113152 | 9/1991 | WIPO . |
| WO9113625 | 9/1991 | WIPO . |
| WO9115224 | 10/1991 | WIPO . |
| WO9116633 | 10/1991 | WIPO . |
| WO9117248 | 11/1991 | WIPO . |
| WO9117444 | 11/1991 | WIPO . |
| WO9118639 | 12/1991 | WIPO . |
| WO9200092 | 1/1992 | WIPO . |
| WO9200751 | 1/1992 | WIPO . |
| WO9200995 | 1/1992 | WIPO . |
| WO9201049 | 1/1992 | WIPO . |
| WO9204442 | 3/1992 | WIPO . |
| WO9206196 | 4/1992 | WIPO . |
| WO9208464 | 5/1992 | WIPO . |
| WO9208472 | 5/1992 | WIPO . |
| WO9208476 | 5/1992 | WIPO . |
| WO9207870 | 5/1992 | WIPO . |
| WO9210199 | 6/1992 | WIPO . |
| WO9209200 | 6/1992 | WIPO . |
| WO9209268 | 6/1992 | WIPO . |
| WO9209293 | 6/1992 | WIPO . |
| WO9212119 | 7/1992 | WIPO . |
| WO9212236 | 7/1992 | WIPO . |
| WO9211367 | 7/1992 | WIPO . |
| WO9211866 | 7/1992 | WIPO . |
| WO9212994 | 8/1992 | WIPO . |
| WO9212727 | 8/1992 | WIPO . |
| WO9212729 | 8/1992 | WIPO . |
| WO9213003 | 8/1992 | WIPO . |
| WO9213887 | 8/1992 | WIPO . |
| WO9217065 | 10/1992 | WIPO . |
| WO9217187 | 10/1992 | WIPO . |
| WO9217188 | 10/1992 | WIPO . |
| WO9217192 | 10/1992 | WIPO . |
| WO9217206 | 10/1992 | WIPO . |
| WO9217498 | 10/1992 | WIPO . |
| WO9217499 | 10/1992 | WIPO . |
| WO9217569 | 10/1992 | WIPO . |
| WO9217604 | 10/1992 | WIPO . |
| WO9218160 | 10/1992 | WIPO . |
| WO9218543 | 10/1992 | WIPO . |
| WO9218610 | 10/1992 | WIPO . |
| WO9218643 | 10/1992 | WIPO . |
| WO9219243 | 11/1992 | WIPO . |
| WO9219269 | 11/1992 | WIPO . |
| WO9219646 | 11/1992 | WIPO . |
| WO9219647 | 11/1992 | WIPO . |
| WO9220337 | 11/1992 | WIPO . |
| WO9220712 | 11/1992 | WIPO . |
| WO9220716 | 11/1992 | WIPO . |
| WO9221240 | 12/1992 | WIPO . |
| WO9222312 | 12/1992 | WIPO . |
| WO9222323 | 12/1992 | WIPO . |
| WO9221363 | 12/1992 | WIPO . |
| WO9222580 | 12/1992 | WIPO . |
| WO9222585 | 12/1992 | WIPO . |
| WO9300107 | 1/1993 | WIPO . |
| WO9300111 | 1/1993 | WIPO . |
| WO9300356 | 1/1993 | WIPO . |
| WO9300357 | 1/1993 | WIPO . |
| WO9300358 | 1/1993 | WIPO . |
| WO9300438 | 1/1993 | WIPO . |
| WO9300908 | 1/1993 | WIPO . |
| WO9300919 | 1/1993 | WIPO . |
| WO9302191 | 2/1993 | WIPO . |
| WO9302698 | 2/1993 | WIPO . |
| WO9305167 | 3/1993 | WIPO . |
| WO9305067 | 3/1993 | WIPO . |
| WO9305150 | 3/1993 | WIPO . |
| WO9305792 | 4/1993 | WIPO . |
| WO9313129 | 7/1993 | WIPO . |
| WO9314782 | 8/1993 | WIPO . |
| WO9315203 | 8/1993 | WIPO . |
| WO9319769 | 10/1993 | WIPO . |
| WO9319783 | 10/1993 | WIPO . |
| WO9320202 | 10/1993 | WIPO . |

DEPOT FORMULATIONS

This is a continuation of application Ser. No. 08/090,079, filed on Jul. 16, 1993, now abandoned.

The present invention relates to compositions which provide prolonged release of wound healing promoters into wounds in humans and animals.

There are four stages which can usually be identified in the natural healing process. Initially the wound is closed so as to limit blood loss and prevent infection. Then damaged tissue is removed and pathogens destroyed by phagocytosis. This is followed by granulation in which the wound is invaded by cell types appropriate to the surrounding tissue and scar formation occurs. Finally the scar tissue is remodelled and changes in the cell population occur resulting in a mature, healed wound. In any particular case variations from this general pattern will occur owing to factors such as the site and type of wound and the condition of the patient, and the details of the process, particularly the later are, as yet, not well understood.

Although very effective in most cases, the natural wound healing process can fail on occasion, or may be unsatisfactory, and medical intervention is desirable. Typical examples of failure include cases of severe burns involving substantial tissue damage where the wounds often not even close completely and where skin grafts are required to secure granulation, cases of leg ulcers where, even when the wounds heal, the healed scar is physically weak and liable to break open very easily and oases where, although a wound would heal naturally, the scarring that remains may be unsightly or cause discomfort. Other wounds which frequently require intervention are serious bone fractures and wounds to cartilage, ligaments and tendons which heal slowly or not at all or where the healed wound will not be sufficiently strong.

Despite considerable work over many years there have been no completely satisfactory treatments for many of these problems in wound healing.

One approach to improving wound healing is the administration of wound healing promoters such as growth factors. However there are many difficulties with this, particularly in ensuring that the agents are delivered to the site of the wound in effective amounts.

The present inventors have developed a depot composition for treatment of wounds wherein the wound healing promoters are concentrated on and released from appropriate binding molecules themselves immobilised on materials comprising binding domains of fibronectin.

Accordingly the present invention provides a depot formulation comprising fibronectin or fragment thereof, a growth factor binding agent linked thereto and growth factor bound to the binding agent.

Fibronectin is a well known and commercially available material. The fibronectin molecule is made up of a number of polypeptide domains, particularly the gelatin-binding domain, the heparin-binding domain and the cell-binding domain. In accordance with the invention fibronectin As used An the intact form or in the form of a fragment thereof, preferably comprising at least one of the foregoing domains. The fibronectin or fragment acts as a targetting entity which assists in delivery of the depot formulation to wound tissue, especially when a cell-binding domain is included.

The growth factor binding agent is a polysulfated polysaccharide such as heparin or heparan sulphate or a polypeptide such as BP53 which specifically binds a growth factor.

Heparin and heparan sulphate are well-known anticoagulants and are commercially available. BP53 is a polypeptide component of serum isolated by known techniques by column fractionation which initially affords a 150 kDA complex that may be dissociated at low pH to give BP53. BP53 may be used as such or in the form of a complex thereof, such as the 150 kDa complex, in the formulations of the invention.

Growth factors useful in the present invention include growth factors, such as fibroblast growth factor (FGF), epidermal growth factor (EGF), endothelial derived growth factor (EDGF), insulin-like growth factor I or II (IGF-I or IGF-II). BP53 is used to bind IGF; heparin and heparan sulphate bind a class of growth factors including FGF, EGF and EDGF.

Preferred depot formulations of the invention comprise fibronectin or a fragment thereof and the growth factor binding agent, especially heparin, in a weight ratio of 5:1 to 100:1, preferably from 20:1 to 50:1.

Without wishing to be bound by this theory the present inventors believe that the growth factors bind to the binding agents such as heparin or BP53 and are effectively presented to cells in or surrounding a wound by the binding agent. By immobilising the binding agent on the fibronectin or fragments thereof, the wound healing promoting agents can be delivered to a wound site, stored there and presented and released to target cells in a prolonged or controlled manner or both to influence and enhance various aspects of wound healing. Moreover, the use of cell-binding domains of fibronectin allows the depot formulation to bind to tissues at or adjacent to the wound site and to be retained in place for the necessary period while wound healing is taking place.

A variety of means are available for linking binding agents such as heparin and BP53 to the fibronectin or fragments thereof. In general, chemical cross-linking using non-deleterious agents and conditions may link the binding agent to the fibronectin. A useful class of chemical cross-linking agents is the carbodiimides which are well known for conjugating materials such as these.

When fibronectin or fragments thereof including the heparin binding domains are used, heparin or heparan sulphate may be bound via the non-covalent interaction With the heparin receptor in the heparin binding domain.

Alternatively the binding agent may be bound to the fibronectin or fragment thereof via carrier material such as polylysine. In this case the fibronectin or fragments thereof and the binding agent are both bound by chemical cross-linking to the carrier material.

Combinations of these techniques may be used such that, for instance heparin or BP53 may be bound by chemical cross-linking to the fibronectin and to a carrier material which is itself cross-linked to the fibronectin. Alternatively, or in addition, heparin-binding domains of fibronectin may be used for non-covalent binding of heparin and heparan sulphate.

Since heparin and heparan sulphate molecules can each bind to more than one heparin binding domain of fibronectin, materials comprising fibronectin or heparin binding domains thereof linked to carriers such as polylysine will be aggregated by heparin or heparan sulphate and can be used to form paste-like formulations.

Preferred depot formulations comprise heparin-binding domains and heparin and are presented as pastes. Other preferred depot formulations comprise cell-binding domains of fibronectin which afford enhanced adhesion between the depot formulations and cells in or adjacent to the would.

In another aspect the invention relates to materials for use in depot formulations as hereinbefore described which materials comprise fibronectin or a fragment thereof and a growth factor binding agent, preferably fibronectin or binding domain fragments thereof and heparin, heparan sulphate or BP53, bound thereto.

These materials may be used to produce depot formulations by contact with a growth factor and capture thereof. This may be achieved by, for instance, perfusing the material with a solution of the agent. In a particularly preferred embodiment the material is perfused with a patient's blood or serum prior to an operation or surgical procedure in order to load the material with wound healing promoting agents from the patient's own circulation (thus avoiding the risks of exogenous blood products). The perfused material absorbs growth factors and can then be used as a depot formulation to aid recovery of the same patient from the operation or surgical procedure.

This mechanism may be exploited by placing the material at the site of the wound, where it will accumulate growth factors from the patient's serum and act as a depot formulation by presenting and releasing the agents to cells in the vicinity of the wound. In addition, depot formulations as previously described will accumulate and release growth factors from the patient's serum whilst releasing the initial growth factors included in the depot formulation prior to implantation, and will continue to do so after the initial growth factors have been consumed.

The present invention further provides materials or depot formulations as hereinbefore defined for use in a method of surgery or therapy practised on the human or animal body. The invention also provides the use of a material or depot formulation as hereinbefore defined in the manufacture of a medicament, dressing or device for use in a method of surgery or therapy practised on the human or animal body. In particular aspects the methods of surgery or therapy involve promoting wound healing or improving the appearance or strength of a healed wound or any combination thereof. The method of surgery or therapy may alternatively involve the growth of autograft material such as skin or ligament promoted by the materials or depot formulations of the invention. When porous macroscopically oriented materials described below are used such growth may be directed by the oriented materials.

The invention further provides a method of treatment of a wounded human or animal comprising applying an effective, non-toxic amount of a material or depot formulation as hereinbefore defined to the wound.

In yet another aspect of the invention, the depot formulations, or materials for use therein comprise porous macroscopically oriented cell adhesion protein as described in a related application filed on even date herewith British Patent Application 9101191.6. That application describes macroscopically oriented cell adhesion protein materials which, surprisingly have been shown to promote wound healing, in particular by creating a scaffolding to which the invading cells can adhere thus facilitating this stage of the wound healing procedure. Moreover, by aligning these materials with features of the wound or surrounding tissue, the cell invasion may be directed along desired orientations thereby strengthening the initial repair and reducing the amount of reorientation required during the remodelling stage. Thus wound healing may be promoted and the mature healed wound can be made stronger or more cosmetically acceptable or both.

In the present invention, these oriented materials may be used as a carrier or substrate for the materials and depot formulations described above. Furthermore, when the materials and depot formulations described above comprise fibronectin, that fibronectin may itself be in the form of porous macroscopically oriented wound treatment material.

It is the orientation of the fibronectin or other cell adhesion protein molecules on a macroscopic scale which is critical to the success of the oriented materials in directing the wound healing process.

The macroscopically oriented cell adhesion protein of the invention comprises large scale aggregates of cell adhesion protein, which self-assemble under favourable conditions as fibrils, the molecules in each individual fibril lying substantially parallel to each other, each individual fibril being oriented over a distance of at least 100 µm and the fibrils being oriented substantially parallel to each other over macroscopic distances such as at least 0.1 m, preferably 0.5 and most preferably for at least 1 mm. Individual fibrils may show orientation over a considerable distance, for instance up to 0.5 mm, possibly up to 1 mm or even for 5 mm or more, for instance 1,2,3 or 5 cm. The aggregate of fibrils may be oriented for over 5 mm or 1 cm or more, for instance 2,3, or 5 cm and, when prepared as a continuous web for subsequent division into individual dressings, the aggregate may be oriented over distances of many centimeters or even many meters.

In a simple embodiment of the invention the fibrils are oriented in a single direction and form a sheet or mat, possibly on a substrate for support, which may be applied to a wound. In more complex embodiments such sheets or mats may be laminated in non-parallel directions, for instance with the fibrils of one layer oriented at 90° to fibrils in a second layer. The fibrils may be arranged into fibres or may be formed on a substrate or oriented by fibres of a substrate, and such fibres may be formed into woven and nonwoven webs having at least one and often two or more orientation directions. When the oriented materials are formed by coating on a substrate, preferably the substrate will be a biodegradable or resorbable material such that it may be left in the wound and will eventually be destroyed as the wound heals or once it has healed or the substrate may be a physical support which is removed after formation of the oriented material.

Cell adhesion proteins useful in these oriented materials include fibronectin, vitronectin and yon Willebrand protean (also called von Willabrand factor) which are well known in the literature. Fibronectin is the preferred cell adhesion protein, preferably substantially pure fibronectin As used. The cell adhesion proteins will usually be provided in sterile, pyrogen-free form.

In use the oriented materials may be applied to wounds to direct and promote the cell invasion and thereby to increase the strength, cosmetic acceptability, healing time or other desirable characteristic of the healed wound. By way of example a simple unidirectionally oriented mat may be used with the orientation direction across the width of a linear wound in order to promote the closing of the wound and enhance the resistance to re-opening of the wound. In another example, more complex webs having multiple orientation directions may be used to promote regrowth of damaged tendons, intervertebral discs and corneas whilst directing adoption by the invading cells of orientations matched to that of the surrounding undamaged tissue or to recreate orientations of the original damaged tissue. Thus the use of the oriented materials will often involve aligning one or more orientation directions of the material with respect to features of the wound or surrounding tissues.

A particular application of the materials of the invention is in stimulation of new capillary growth, a frequently perceived objective for many forms of wound repair. Classically, the approach has been to attempt to stimulate angiogenesis generally, using a diffusible factor. However, one part of the process of angiogenesis is endothelial cell adhesion to and migration over the substrate matrix. A development of the present invention can be applied to this by promoting attachment/migration of capillary cells to discrete fibres or strands. These strands would be orientated in the direction of the required capillary growth. Strands can take the form of (i) materials of the invention comprising fibronectin in macroscopic fibrous form; (ii) materials of the invention comprising Fn strands laid into conventional wound implant materials (e.g. gelatin or modified cellulose sponges); (iii) materials of the invention comprising fibronectin coated on braided resorbable sutures. Whether formed of oriented Fn or fibronectin coated, the individual strands should be less than 200 μm wide (ideally between 1 and 100 μm. These structures form excellent support and adhesion substrates for repair cells In a further modification (particularly of the Fn-coated, braided suture) it is possible to incorporate a chemotactic stimulus by attaching a solid, growth factor containing gel to one end of the suture. A natural example of such a "gel" would be a blood or plasma clot (ideally prepared from the patient's own blood). Artificial substrates based on gelatin (or other gel-forming material) containing the required new vessels would grow towards the end bearing the gel or angiogenic factor could also be used. This suture would be drawn through or across the damaged tissue in such a way that clot. This form of suture may usefully be employed as an "angiogenic track" during repair of avascular or poorly vascular tissues such as torn menisci, ligaments or tendons.

Materials for use in the invention whether oriented or not may further comprise additional therapeutic agents, for instance agents which promote wound healing such as growth factors and growth hormones, clotting factors, platelet adhesion promoters such as thrombin; agents which promote calcification; collagen; fibrinogen; antimicrobial agents and heparin.

The fibrils and materials may be used as formed or stabilised by cross-linking using chemical reagents such as glutaraldehyde or enzymes such as factor XIIIa, which is a transglutaminase. Cross-linking with other components such as collagen and fibrinogen, for instance using a transglutaminase, is also contemplated. Where the materials include collagen and/or fibrinogen it is preferred for these also to be oriented substantially parallel to the fibrils of oriented cell adhesion protein.

Preferably the materials are used as, or as part of, a wound dressing, or are applied to open wounds separately from a conventional dressing. To derive improved strength and/or cosmetic acceptability of the mature wound it is preferred that the materials are oriented and are applied to the wound with an orientation direction aligned with features of the surrounding tissues so as to encourage invasion along the orientation direction. For instance, the fibres may be aligned with muscle fibres in the wound or underlying tissue, across a linear wound or parallel with or at right angles to directions in which a tissue will be strained once healed.

Macroscopically oriented materials are produced by forming and orienting fibronectin fibrils from solution and removing the solvent.

Solvents useful in this process are generally aqueous solvents such as buffered water, distilled water, demineralised water and pyrogen-free water. The solvent may contain additional solutes and/or suspended particles for inclusion in or deposition on the fibronectin materials.

The solvent may be removed by evaporation, filtration concentration or by aggregating or precipitating the fibronectin using, for instance, appropriate concentrations of salts or by adjusting the pH of the solution to acidic or basic pH and collecting and drying the aggregate or precipitate. The oriented materials are preferably washed and dried and may be optionally stabilised, for instance by chemical cross-linking using reagents such as glutaraldehyde or enzymatically using factor XIIIa.

The cell adhesion protein may be oriented by self-association from solution, preferably a high concentration solution at 0.7 mg/ml or greater, for instance greater than 1 mg/ml such as at least 1.5 mg/ml, for instance 2 mg/ml or more or even up to 3 mg/ml or more at about neutral pH to form fibrils on solid surfaces which fibrils are sufficiently stable to be handled, recovered and dried. Use of a solution at about 1.5 mg/ml is most preferred. A pH of about 7.6, eg using tris-HCl buffer has been found convenient. Preferably the solution contains soluble ionic compounds to increase the ionic strength thereof, especially in the range up to 0.5M ionic strength. Preferably the solution also contains urea at preferably 1 to 3M. A combination of fibronectin, urea at 2M and 0.1 to 0.5M sodium chloride is preferred. Thus, for example, fibronectin may be oriented by applying continuous unidirectional motion, such as by stirring, to a saturated solution and removing the solvent so as to precipitate oriented fibronectin, for instance on the stirrer. This may be recovered and blotted to form mats which may be laminated in parallel or non-parallel directions; to form a lattice. Alternatively, high concentration solutions may be drawn into fibres and the solvent removed leaving fibronectin fibres comprising oriented fibrils. A preferred technique for drawing fibres involves dipping an applicator onto the surface of the solution and lifting the applicator to produce one or more fibres under the effects of surface tension. A preferred material for the applicator is the mineral mica. In a further alternative, a concentrated solution of fibronectin is applied to a fibrous substrate and the solvent is removed.

Heparin can be incorporated into the fibronectin solution (preferably at ratios of 1:5 to 1:100, by weight heparin:Fn) without impairing its ability to form strands. However, after drying, strands made with higher heparin ratios (eg 1:5, heparin:Fn) were flat, with very little mass as a result of the high level of hydration of the newly formed strands due to the heparin content.

Macroscopically oriented fibronectin may be cross-linked with heparin and/or BP53 carrier materials and have wound-healing promoting agents bound thereto as previously described for other forms of fibronectin and fragments thereof.

The invention will now be illustrated by the following Examples which are not intended to limit the scope of protection in any way.

EXAMPLE 1

A solution of human plasma fibronectin purified by gelatin affinity chromatography (approx 1.0 (eg 0.5 to 1.5) mg/ml) in neutral pH buffer (10 mM phosphate or 20 mM Tris HCl pH7.5) containing 0.15M sodium chloride is placed into a pressurized "stirred cell" concentration device with an ultra filtration membrane (molecular weight cut off approx. 10 to 20,000 Daltons: eg Amicon PM 10 membrane). Such a stirred cell (eg 100 ml capacity) is operated at a preferred pressure of 25 psi (range approx. 10 to 75 psi) under nitrogen or under air with a stirring rate of approx 300 rpm (range 50 to 600 rpm) at 4° C. The volume is slowly reduced under these conditions to less than half the initial volume giving a fibronectin concentration within the cell of approx 3 mg/ml (range of 2.0 to 10 mg/ml). The conditions for selfaggregation will vary depending on the purity and integrity of the fibronectin starting material, but within these ranges, a large clot or mat of solid fibronectin will be formed on the stirring bar of the cell. This can be removed and fresh fibronectin solution added to permit the formation of more fibronectin matting.

EXAMPLE 2

A starting solution as described in Example 1 but containing over 1 mg/ml of fibronectin (Fn) at a pH around neutrality sodium chloride concentration up to 0.2M is prepared. A suitable flat edged "applicator" (for example a 2 cm glass cover slip) is dipped into the solution to a depth of at least 3 mm. This same wetted edge is now touched onto a hydrophilic surface (e.g. flat plastic culture dish) forming a small pool of the Fn solution, clinging to both the "applicator" and the surface. When the applicator is slowly lifted off the surface to be coated, a single strand of protein forms between the "applicator" and "surface" under the effect of surface tension. This strand of protein (spanning between surface and applicator) can be pulled across the surface for 2 to 5 mm and re-attached to the surface by again touching the applicator and the surface. The resultant strand of protein is firmly attached to the surface by multiple subdivided fibrils at either end. They are commonly 2 to 5 μm in diameter and up to 5 mm long. They are stable with or without chemical cross linking (e.g. with glutaraldehyde) and can be washed and dried without becoming dislodged. Their orientation on the "surface" can be controlled precisely.

In cell culture tests, strands of pure fibronectin promoted a directional orientation and attachment of fibroblasts in spite of the presence of soluble fibronectin. Stands of fibronectin were still visible in such cultures after 24 hrs exposure to fibroblasts.

EXAMPLE 3

Examples of the application of depot forming conjugates to achieve regulated delivery of locally acting growth factors. Note: the means of delivery of the depot need not be specific to this application and so other quite different techniques could be applied.

The form of the depot in these examples goes from soluble to a paste and finally to a mat, as the proportion of the fibronectin molecule used is increased.

1. The gelatin binding domain of fibronectin (Fn GBP) is linked (chemically) to heparin or BP53 or both. This soluble complex binds the required growth factor(s) and also targets the material towards sites of connective tissue damage (ie wounds). The ratio of the growth factor to Fn GBP should be greater than 2:1 (molecular basis) and ideally greater than 10:1. These levels may be achieved using a carrier polylysine.
2. The heparin binding domain of fibronectin (Fn HBD) is used alone is with no other activity, or as large fragments which include heparin binding domain and also include cell or gelatin binding domains or both. FnHBD is crosslinked to commercial polylysine (high molecular weight) and mixed with heparin with which it interacts to form large, precipitating aggregates. The resulting precipitate is used to form a depot formulation for application to wound sites, favouring cell attachment.
3. The macroscopically oriented fibronectin materials described elsewhere form the basis, or carrier, for the depot-forming conjugates in this example. In this case heparin or BP53 or both are cross-linked, either directly or (preferably) through a spacer, for example polylysine. Thus the surface of the fibronectin fibrilar matting carries conjugates of heparin and/or BP53 which in turn can be reversibly loaded with growth factors An the way described above.

EXAMPLE 4

Mats were prepared as described in Example 1 using a stirred cell, under a range of conditions to test for preferred composition of the starting fibronectin solution. Mat formation was assessed on the basis of the dry weight of mat recovered and uv. absorbance (at 280 nm) of the fibronectin solution at the start and end of the mat forming process. Fibronectin solutions made to 2M with urea were found to be preferable, giving a greater % mat formation at the same ionic strength.

The ionic strength of the Fn solution was raised in increments, using greater concentrations of sodium chloride from zero to 1.0M, and the recovery of Fn as a mat (as % of total Fn in solution) was measured. From data on the relationship of sodium chloride concentration to % Fn incorporation to the mat, it is clear that mat formation is adequate between 0.1M and 0.5M sodium chloride with a preferred concentration of 0.1M sodium chloride.

EXAMPLE 5

The influence of heparin, in the starting solution of Fn, was tested on the quantity and quality of mats formed in the "stirred cell" (see Example 1). As in Example 4, the efficiency of mat production was measured as % Fn incorporated into the aggregate. Heparin was added to known concentrations of Fn solution at ratios (weight:weight) from 1:15 to 1:200 (heparin:Fn). Heparin was from the Sigma Chemical Co., Poole, Dorset, U.K. Each mat was made under otherwise identical conditions, from solutions of Fn containing 0.1M sodium chloride, 2M urea, 50 mM tris-HCl pH7.6. At ratios below 1:15 (Heparin:Fn) mat formation was largely or wholly inhibited. Beyond a ratio of 1:40 there was little change. The preferred ratio is 1:20 to 1:40. Heparin incorporation into the mat (measured by the "Methylene Blue" assay for glycosaminoglycans) was determined at approx. 20 μg/mg of Fn, using a starting solution Heparin:Fn ration of 1:15. This represents an incorporation rate of 30%. In general mats containing heparin had a poorer orientation than those prepared without. All of these materials, when dried, were convenient materials to place into wounds in a variety of tissues, rehydrating to form solid proteinaceous deposits in solutions at physiological ionic strength and pH.

We claim:

1. A formulation comprising fibronectin or a fragment thereof, which comprises a gelatin-binding domain or a heparin-binding domain of fibronectin, the fibronectin or fragment thereof having a growth factor binding agent immobilized thereon and a growth factor releasably bound to the binding agent, and wherein the fibrils of the fibronectin or fragment thereof are in the form of a porous macroscopically oriented material.

2. A formulation according to claim 1 wherein the fibronectin or fragment thereof further comprises a cell-binding domain of fibronectin.

3. A formulation according to claim 1 wherein the growth factor binding agent is a polysulphated polysaccharide or a polypeptide which specifically binds a growth factor.

4. A formulation according to claim 3 wherein the polysulphated polysaccharide is heparin or heparan sulphate.

5. A formulation according to claim 3 wherein the polypeptide growth factor binding agent is BP53.

6. A formulation according to claim 1 wherein the growth factor is fibroblast growth factor, epidermal growth factor, endothelial derived growth factor or insulin-like growth factor I or II.

7. A method of treating a wound which comprises applying an effective, non-toxic amount of a formulation according to claim 1 to the wound.

8. A method of treating a wound, comprising the steps of:
 a. applying an effective amount of a formulation according to claim 1 to heal a wound and
 b. allowing the wound to heal while in contact with the formulation thereby promoting wound healing, improving the appearance or strength of a healed wound, or promoting or directing the growth of autograft material.

9. The method of claim 8 wherein the growth factor binding agent is a polysulphated polysaccharide or a polypeptide whch specifically binds a growth factor.

10. The method of claim 9 wherein the growth factor binding agent is heparin or heparan sulphate.

11. The method of claim 8 wherein the gowth factor binding agent is BP53.

12. The method of claim 8 wherein the growth factor is fibroblast growth factor, epidermal growth factor, endothelial derived growth factor or insulin-like growth factor I or II.

13. A material for use in producing a formulation according to claim 1, comprising fibronectin or a fragment thereof which comprises a gelatin-binding domain or a heparin-binding domain of fibronectin, the fibronectin or fragment thereof having a growth factor binding agent immobilised thereon and wherein the fibrils of the fibronectin are oriented to form a porous unidirectional and macroscopic mat.

14. A material according to claim 13, wherein the fibronectin or fragment thereof further comprises a cell-binding domain of fibronectin.

* * * * *

UNITED STATES PATENT AND TRADEMARK OFFICE
CERTIFICATE OF CORRECTION

PATENT NO. : 5,629,287

DATED : May 13, 1997

INVENTOR(S) : BROWN et al.

It is certified that error appears in the above-identified patent and that said Letters Patent is hereby corrected as shown below:

On the Title page, item [63]:

Continuation of Ser. No. 90,079, Jul. 16, 1993, abandoned, filed as PCT/GB92/00101, Jan. 17, 1992.

Signed and Sealed this

Seventh Day of April, 1998

*Attest:*

BRUCE LEHMAN

*Attesting Officer*    Commissioner of Patents and Trademarks